US00RE41666E

(19) United States
(12) Reissued Patent
Simon et al.

(10) Patent Number: US RE41,666 E
(45) Date of Reissued Patent: Sep. 14, 2010

(54) PROCESS AND ARRANGEMENT FOR CONFOCAL MICROSCOPY

(75) Inventors: Ulrich Simon, Jena (DE); Sebastian Tille, Danbury, CT (US); Gunter Moehler, Jena (DE); Stefan Wilhelm, Jena (DE); Ulrich Meisel, Jena (DE); Ernst Stelzer, Meckesheim (DE)

(73) Assignees: Carl Zeiss Jena GmbH, Jena (DE); European Molecular Biology Laboratory, Heidelberg (DE)

(21) Appl. No.: 10/959,949

(22) Filed: Oct. 7, 2004

Related U.S. Patent Documents

Reissue of:
(64) Patent No.: 6,462,345
Issued: Oct. 8, 2002
Appl. No.: 09/295,556
Filed: Apr. 21, 1999

(30) Foreign Application Priority Data

Jul. 4, 1998 (DE) ..... 198 29 981

(51) Int. Cl.
*G01N 21/64* (2006.01)
*G01J 3/30* (2006.01)

(52) U.S. Cl. ..... 250/458.1; 356/318

(58) Field of Classification Search ..... 250/458.1, 250/459.1, 461.1, 461.2; 356/317, 318, 417
See application file for complete search history.

(56) References Cited

U.S. PATENT DOCUMENTS

| | | | | |
|---|---|---|---|---|
| 5,127,730 | A | 7/1992 | Brelje et al. | |
| 5,294,799 | A | 3/1994 | Aslund et al. | |
| 5,675,155 | A * | 10/1997 | Pentoney et al. | 250/485.1 |
| 6,020,591 | A | 2/2000 | Harter et al. | |
| 6,341,036 | B1 * | 1/2002 | Tearney et al. | 359/368 |
| 6,462,345 | B1 * | 10/2002 | Simon et al. | 250/458.1 |

(Continued)

FOREIGN PATENT DOCUMENTS

| | | |
|---|---|---|
| DE | 39 41 726 A1 | 9/1990 |
| DE | 39 15 692 | 11/1990 |
| DE | 691 31 176 | 2/1992 |
| DE | 694 02 958 T2 | 12/1997 |
| EP | 0 440 342 A2 | 8/1991 |
| EP | 0 620 468 | 10/1994 |
| EP | 0 782 027 | 2/1997 |
| EP | 0 916 981 | 2/1999 |
| WO | WO 94/18547 | 8/1994 |

OTHER PUBLICATIONS

Thomas Hubin et al., "An acousto–optically scanned video–rate confocal microscope suitable for use with multiple wavelengths" 12434 *Three–Dimensional Microscopy: Image Acquisition and Processing*, Feb. 7–8, 1994, San Jose, CA, US 2184 (1984) Bellingham WA, US.

(Continued)

*Primary Examiner*—David Porta
(74) *Attorney, Agent, or Firm*—Jacobson Holman PLLC

(57) ABSTRACT

A process for confocal microscopy [is disclosed] in which laser light is coupled into a microscope beam path, directed successively with respect to time onto different locations of a specimen, and an image of the scanned plane is generated from the light reflected and emitted by the irradiated locations. A change in the spectral composition and in the intensity of light [is] *are* carried out during the deflection of the laser beam from location to location, while the deflection continues in an uninterrupted manner[. In this way], *so that* at least two *adjacent* locations of the specimen [located next to one another] are acted upon by light with different spectral characteristics and by laser radiation of different intensity. By periodically interrupting the coupling in of the laser light during the deflection of the microscope beam path, [it is made possible that] only selected portions of the image field are acted upon by the laser radiation. A laser scanning microscope for carrying out this process is also disclosed. *A laser scanning microscope for carrying out this process is also disclosed.*

42 Claims, 2 Drawing Sheets

U.S. PATENT DOCUMENTS

| | | | | | |
|---|---|---|---|---|---|
| 6,496,307 | B2 | * | 12/2002 | Engelhardt et al. | 359/389 |
| 6,548,796 | B1 | * | 4/2003 | Silvermintz et al. | 250/201.3 |
| 6,603,537 | B1 | * | 8/2003 | Dietz et al. | 356/39 |
| 6,924,490 | B2 | * | 8/2005 | Natori | 250/458.1 |
| RE38,860 | E | * | 11/2005 | Shimada | 250/234 |
| 6,995,841 | B2 | * | 2/2006 | Scott et al. | 356/318 |
| 7,038,848 | B2 | * | 5/2006 | Nakata et al. | 359/386 |
| 7,130,043 | B2 | * | 10/2006 | Natori | 356/318 |
| 2003/0151742 | A1 | * | 8/2003 | Silvermintz et al. | 356/318 |
| 2006/0012871 | A1 | * | 1/2006 | Funk et al. | 359/385 |

OTHER PUBLICATIONS

Laura Robinson et al, "Confocal microscopes probes biological specimens" (Original article published in *Laser Focus World*), May 1994, pp. 215–220.

P. Wedekind et al., "Scanning Microphotolysis: A New Photo–Bleaching Technique Based on Fast Intensity Modulation Of A Scanned Laser Beam And Confocal Imaging, " *Journal of Microscopy*, vol. 176, Pt. 1, Oct. 1994, pp. 22–33.

X. Wang et al., *Fluorescence Imaging Spectroscopy and Microscopy*, John Wiley & Sons 1996, Chapter 5, pp. 125–156.

P. Wedekind et al, "Line–Scanning Microphotolysis For Diffraction–Limited Measurements of Lateral Diffusion, " *Biophysical Journal*, vol. 71, Sep. 1996, pp. 1621–1632.

K. Carlsson et al., "Using intensity–modulated scanning beams in combination with lock in detection for recording multiple–labeled fluorescent specimens in confocal laser microscopy, " *SPIE vol. 2184 Three–Dimensional Microscopy*(1994), pp. 21–29.

Technische Daten LSM 510 (Release 2.8) 1997 XP002173907, and English language abstract.

R. Nitschke, u.a., "A modified confocal laser scanning microscope allows fast ultraviolet ratio imaging of intracellular Ca2+activity using Fura–2", In Pflügers Arch—Eur J Physiol (1997) 433:653–66.

K. Winkler, W. Knebel, "Leica TCS 4D UV—Das Systemkonzept für die Multiparameter–Konfokalmikroskopie", in Mitteilungen für Wissenschaft und Technik Bd. XI. Nr. 1, S. 9–19 Jun. 1995.

* cited by examiner

PROCESS AND ARRANGEMENT FOR CONFOCAL MICROSCOPY

Matter enclosed in heavy brackets [ ] appears in the original patent but forms no part of this reissue specification; matter printed in italics indicates the additions made by reissue.

BACKGROUND OF THE INVENTION a) Field of the Invention

The invention is directed to a process for confocal microscopy in which laser light of different spectral ranges is coupled into a microscope beam path deflected in at least two coordinates and is directed successively with respect to time onto locations of a specimen, wherein the specimen is acted upon, location by location and line by line, by the laser light in at least one plane and an image of the scanned plane is generated from the light reflected and/or emitted by the irradiated locations. The invention is further directed to a laser scanning microscope for carrying out this process.

b) Description of the Related Art

While conventional light microscopy only enables the optical acquisition of one imaging plane, confocal microscopy, as a special further development of light microscopy, offers the possibility of imaging and measuring microstructures also in the Z spatial axis. With light microscopy, it is not possible, for example, to gain an impression of the spatial structure of the rough surface of a specimen at high magnification because only a small area of the specimen can be shown in sharp focus, while details located deep in the surface are imaged in a blurry manner because of the high scattered light component and deficient axial resolution.

In confocal laser scanning microscopy, on the other hand, the scattered light is extensively eliminated and only the structures located in the focal plane of the objective are imaged. If the radiation is focused on different planes, three-dimensional images of a specimen can be calculated from the scanning of these planes which are staggered in the direction of the Z-axis.

For this purpose, a first pinhole is imaged in the object plane so as to be reduced in a punctiform manner using lasers as an illumination source. The punctiform laser beam is moved over the specimen in a raster pattern from location to location and line by line by means of deflecting mirrors. The light reflected and/or emitted by the specimen is focused through the microscope objective onto a second pinhole which is arranged so as to be conjugated with respect to the first pinhole. As a result of the arrangement of these two pinholes, only information from the focal plane reaches one or more detectors which are arranged following the second pinhole.

The scattered light occurring above and below the focus is eliminated by the second pinhole. The information determined by two-dimensional deflection from a plurality of imaging planes located one above the other is stored and subsequently processed to form images.

This principle of confocal laser scanning microscopy is described, for example, in Schroth, "Konfokale Laser-Scaning-Mikroskopie, eine neue Untersuchungsmethode in der Materialprüfung [Confocal Laser Scanning Microscopy, a new method of investigation in materials testing]", Zeitschrift Materialprüfung, volume 39 (1997), 6, pages 264 ff.

Further, it is known from "Mitteilungen für Wissenschaft und Technik", volume II, no. 1, pages 9–19, June 1995, to use either individual lasers, each having one wavelength, or "multi-line" mixed gas lasers with a plurality of usable wavelengths as illumination source in laser scanning microscopes. This opens up the possibility of utilizing confocal microscopy for fluorescence technique in addition to the classic contrasting processes of bright field, phase contrast and interference contrast. The basis for this consists in that different fluorochromes whose excitation and emission wavelengths lie in different spectral regions allow structures to be shown in a plurality of fluorescence colors simultaneously. Accordingly, depending on the spectral characteristics of different dye molecules, conclusions may be reached about physiological parameters in addition to morphological information. When the confocal microscope is used for fluorometric processes, information can be derived concerning changes in the concentration of ions and molecules. In this connection, other important indicators are those which show a shifting of the excitation and emission spectrum in addition to the intensity dependence and, in this regard, enable a quantification of ion concentrations. Also proposed in this connection is the photobleaching method in which a defined nonuniformity is generated in order to be able to obtain information about the object such as fluidity and diffusion through the dynamics of the equilibrium which is subsequently initiated.

It is known from the above-cited publication to use Ar-Kr lasers for fluorescence excitation in the visible spectral region with lines 488 nm, 568 nm and 647 nm. These lines are combined in a laser beam and supplied to the scanning device via light-conducting fibers. An Ar laser with wavelengths 351 nm and 364 nm is suggested for excitation in the UV range. Coupling into the scanning device is also carried out in this instance via light-conducting fibers.

The processes and arrangements described herein can be utilized for acquiring 3D data records which allow, for example, a reliable correlation of spatial cell structures and tissue structures within a microarchitecture or the localization of a plurality of gene sites in chromosomes in FISH experiments.

However, a disadvantage consists in that the respective specimen is acted upon over the entire scanning region by the laser radiation that is generated in the laser module and coupled into the scanning unit. The entire scanning region is therefore exposed to a relatively high radiation loading which leads to unwanted effects and insufficient results particularly when investigating living organisms.

A further disadvantage consists in that radiation emitted and/or reflected from a determined location on a specimen cannot be detected and evaluated in a definite manner when the specimen is excited with different wavelengths such as those of the above-mentioned laser lines, since the "bleed-through" effect occurs between the individual spectral lines.

OBJECT AND SUMMARY OF THE INVENTION

On this basis, the primary object of the invention is to further develop a process for laser scanning microscopy of the type described above in such a way that the radiation loading of the specimen is reduced and a more precise image evaluation is achieved.

According to the invention, this object is met in that a change in the spectral composition and/or in the intensity of light is carried out during the deflection of the laser beam from location to location. This is effected either in that the coupling in of individual spectral components or of a plurality of spectral components or the radiation of the light in its entirety is periodically interrupted or in that individual spectral components or a plurality of spectral components are periodically coupled into the microscope beam path additionally, while the deflection of the microscope beam path continues in an uninterrupted manner.

In this way, at least two locations located next to one another on the specimen are acted upon by light with different spectral characteristics and/or by laser radiation of different intensity. By periodically interrupting the coupling in of the laser light during the deflection of the microscope beam path, it is made possible that only selected portions of the image field are acted upon by the laser radiation.

The specimen is protected in that only the areas of the specimen relevant for image evaluation are acted upon by laser radiation of high intensity.

In a preferred construction variant of the process according to the invention, the spectral composition and/or intensity of the laser light is changed during the scanning of a plurality of locations which are located adjacent to one another and thus form a scanning line. In this connection, the deflection can be carried out over the locations of this line repeatedly in the same direction or also bidirectionally. It is provided according to the invention, for example, that the change in the spectral composition or in the intensity is always carried out with reference to the same locations lying adjacent to one another in this line during every scan over the locations in this line, regardless of whether this scan is carried out in the same direction or in the opposite direction, so that the quality of the image evaluation is increased while the energy introduced into the specimen remains limited. In this way, it is achieved at the same time that individual adjacent locations of the specimen can be observed without bleed-through of individual spectral regions into one another.

The different spectral composition of the laser radiation coupled into the microscope beam path is achieved, for example, in that the radiation provided by a plurality of line lasers, e.g., with wavelengths of 633 nm, 568 nm, 543 nm, 514 nm, 488 nm and 458 nm, is coupled in as required or depending on the characteristics of the specimen to be evaluated with an individual wavelength, with a selection of a plurality of individual wavelengths or with all available individual wavelengths. In addition to this radiation in the VIS range, additional wavelengths in the UV range, for example, 351 nm and 364 nm, can be provided for coupling in.

In preferred constructions of the invention, the laser radiation is coupled into the microscope beam path via single-mode fibers so as to maintain polarization. The respective laser lines provided for radiation are advantageously adjusted to a desired brightness with an acousto-optic tunable filter (AOTF) which can also be followed by an acousto-optic modulator (AOM). The respective laser wavelength is adapted to the microscope objective placed in the beam path for both the UV and the VIS region by variable beam collimation.

A further preferred construction of the process according to the invention consists in that the light reflected and/or emitted by every individual irradiated location of the specimen is evaluated with respect to its spectral characteristics and intensity, wherein the evaluation is carried out synchronously with the irradiation of the same location and while taking into consideration the spectral composition and/or intensity of the laser light by which this location is irradiated. This makes it possible to evaluate the scanned portion of the specimen with respect to individual locations, which leads to a very high resolution and to the highest possible accuracy in the evaluation of the image.

It also lies within the framework of the invention that the laser light reflected and/or emitted by every individual irradiated location is detected with a plurality of detection channels, wherein the individual detection channels are arranged for receiving different spectral components. This provides very good conditions for the examination of multifluorescence specimens, and identical optical sections can be generated via every detection channel with simultaneous reception of multifluorescence specimens.

In this connection, it is provided according to the invention that the spectral composition and/or the intensity of the laser light which is coupled into the microscope beam path corresponds to the excitation radiation of a fluorescence dye contained in the specimen or applied to the specimen and the individual detection channels are configured for the reception of the emission radiation proceeding from the fluorescence dye. This makes it possible to generate laser light for the excitation of different fluorescence dye and to draw conclusions from the detection concerning the distribution of these fluorescence dyes on or in the specimen.

Another very preferable construction of the invention consists in that an evaluation of the spectral composition and/or of the intensity of the coupled in laser light is carried out in a continuous manner and the evaluation findings for the laser radiation directed to a determined location are mathematically linked with the evaluation findings for the light reflected and/or emitted by this location. As a result of this link, for example, the deflection position of the microscope beam path for two adjacent locations can be determined according to the coordinates x, y, z for which differences in the spectral characteristics of the light reflected and/or emitted from these locations which go beyond a predetermined threshold value can be detected during evaluation, wherein, based on these differences, conclusions can be reached concerning the presence of an optical boundary layer between these two locations. These deflection positions are stored, according to the invention, and taken as a basis for the calculation of surface areas and/or volumes enclosed by optical boundary layers within the specimen.

Further, with the deflection positions which are obtained and stored in this way, it is possible to determine and preset adjustment signals for the spectral composition and/or the intensity of the laser light for irradiation of these locations during a subsequent scan cycle, so that an automatic optimization is achieved in the image evaluation while taking into account the optical characteristics of the specimen and of the fluorescence dye.

In particular, the process according to the invention can be used in an advantageous manner for photobleaching, as it is called. In this connection, a selected area of a specimen can be acted upon initially by a relatively high radiation intensity during scanning, thereby initiating a bleaching process. With the scan cycles following immediately thereafter, the reactions taking place are optically detected and evaluated, wherein information can be obtained about the dynamic processes such as diffusion and transport processes taking place in the specimen substance immediately after the bleaching process.

For this purpose, the scanning must be carried out with a very high time resolution, which is achieved, according to the invention, by switching between different intensities and different spectral compositions of the light impinging on individual locations of the specimen, wherein this switching is carried out with sufficient speed in a synchronous manner with respect to the deflection of the beam.

The fast switching between different intensities and different spectral compositions of the laser radiation is carried out with an acousto-optic tunable filter (AOF) which, in an analogous but substantially faster manner, takes over the function of different filters which can be substituted for one another in the beam path and which, further, can also modulate the intensity of individual laser lines or optional combinations of lines in a highly dynamic manner with respect to time.

The manner of operation and application of the AOTF is thoroughly described, for example, in String, Kenneth, R., "Wavelength Selection for Illumination in Fluorescence Microscopy", NIH, LKEM, Building 10/6N309, Bethesda, MD 20892, April 1993. Further, concrete application examples for the AOTF are described in U.S. Pat. Nos. 5,444,528, 5,377,003 and 5,216,484.

The synchronization in time between the driving of the AOTF for modulation of the laser radiation and the driving of the scanning device for beam deflection is achieved in that determined control signals for the AOTF are correlated with the control signals supplied to the scanning device by the driving device. Thus, the scanning device and AOTF are always driven synchronously, i.e., the control pulses for the AOTF are, with respect to time, always added to the output of a control pulse for the scanning device.

On the other hand, this means that a characteristic intensity and/or spectral composition of the light can be assigned to every deflection position and accordingly to every location of the specimen.

In this respect, the circuit arrangements for executing the process are optimized by the AOTF with respect to very short transit times of the control pulses from output to switching of beam modulation. These transit times are in the range of <10 ms. In a variant of the process, when controlling the AOTF or the scanning device, rate action times or lead times are calculated beforehand for switching the intensity and spectral composition and/or for deflection, so that precisely the intended location is also irradiated with the intended radiation intensity and spectral composition.

The invention is further directed to a laser scanning microscope for carrying out the process steps described above, with a laser module for generating laser light with different selectable spectral components, with single-mode fibers for coupling the laser light into the microscope beam path, with a scanning device which deflects in at least two dimensions, with a microscope objective which focuses the laser light on a specimen, with a plurality of detectors for the reception of different spectral components of the light reflected and/or emitted by the specimen, and with an evaluation circuit which is connected subsequent to the outputs of the detectors.

In a laser scanning microscope of this kind, according to the invention, a plurality of individually controllable single-wavelength and/or multiple-wavelength lasers are provided in the laser module, the laser module is followed by a beam combiner, an acousto-optic tunable filter (AOTF) and/or an acousto-optic modulator (AOM), the single-mode fiber is followed by collimating optics whose distance from the respective end of the fiber can be changed and which are coupled with drivable adjusting devices. Photomultipliers (PMT) are provided as detectors, each of which is associated with a reflection band or emission band and accordingly with a detection channel. Filters and/or color splitters which are arranged on splitter wheels and which can be substituted for one another by rotating the splitter wheels are provided for branching the radiation proceeding from the specimen into individual detection channels, wherein every splitter wheel is likewise coupled with a controllable adjusting device. Further, the control inputs of the laser module, AOTF, AOM, scanning device and adjusting devices for the splitter wheels and collimating optics are connected with the outputs of the evaluation circuit.

In a construction variant of the laser scanning microscope, the microscope beam path directed on the specimen is branched and one of the branches is directed to an optoelectronic receiver whose output is likewise connected with the driving unit.

Further, it is provided in a preferred construction variant that a mathematical linking of the output signals of the optoelectronic receiver with the output signals of the PMT and/or with the deflection signals for the scanning device is carried out in the evaluation circuit, wherein optimized adjusting signals for the laser module, AOTF, AOM, scanning device and for the adjusting device are made available at the output of the evaluation circuit.

The invention will be explained more fully hereinafter with reference to an embodiment example.

DESCRIPTION OF THE PREFERRED EMBODIMENTS

Figure 1:
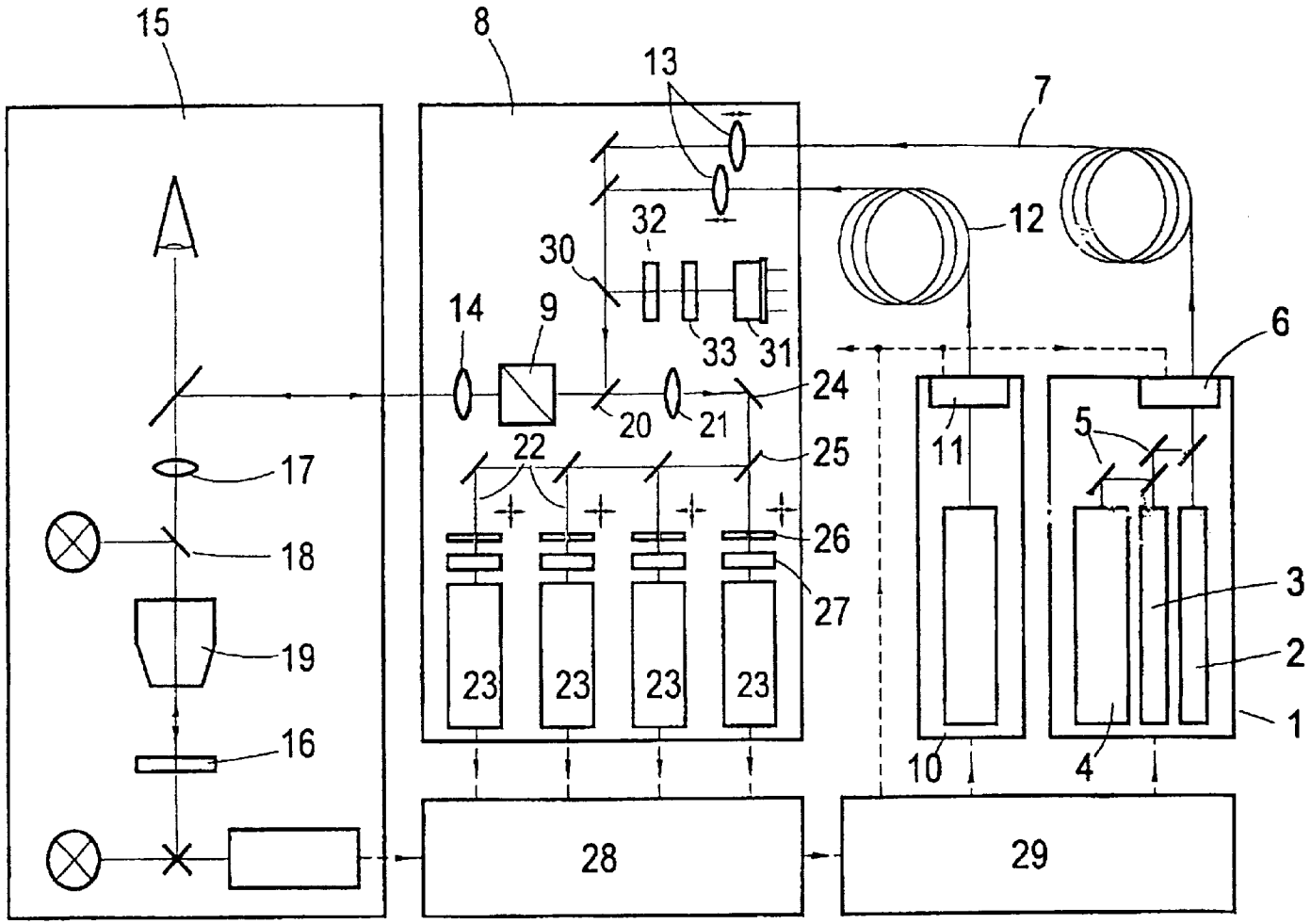
FIG. 1 shows the basic construction of a laser scanning microscope.

FIG. 1 shows a laser module 1 which is outfitted with lasers 2, 3 and 4 for generating laser light in the visible range with wavelengths of 633 nm, 543 nm and 458 nm. By mean of a plurality of beam combiners 5, an AOTF 6 and a fiber 7, the radiation emitted by these lasers is coupled into a scanning device 8 which is outfitted with a unit 9 deflecting beams in the x and y coordinates.

A UV laser whose light is coupled into the scanning device 8 via an AOTF 11 and a light-conducting fiber 12 is provided in a second laser module 10.

In the two beam paths, collimating optics 13 are provided subsequent to the light-conducting fibers 7 and 12, wherein the distance between the collimating optics 13 and the respective end of the fiber can be changed and the collimating optics 13 are coupled for this purpose with a controllable adjusting device (not shown in the drawing).

The laser radiation is coupled into the beam path of the schematically shown microscope 15 by the beam-deflecting device 9 through a scanning objective 14 and is directed on a specimen 16. For this purpose, the laser radiation passes through a tube lens 17, a beam splitter 18 and the microscope objective 19.

The light returned (reflected and/or emitted) by the irradiated location at the specimen travels back through the microscope objective 19 to the beam-deflecting device 9, then passes through a beam splitter 20 and, after being branched into a plurality of detection channels 22, is directed by the imaging optics 21 onto photomultipliers 23, each of which is associated with a detection channel 22. For the purpose of branching into the individual detection channels 22, the light is directed from a deflection prism 24 to dichroitic beam splitters 25. Emission filters 27 and pinholes 26 are provided in every detection channel 22, wherein the latter are adjustable in the direction of radiation and vertical thereto and also in diameter.

The outputs of the photomultipliers 23 lead to the signal inputs of an evaluation circuit 28 which is connected in turn with a driving device 29. The outputs of the driving device 29 are connected with the signal inputs of the laser modules 1 and 10 and with signal inputs of the adjusting devices for influencing the position of optical elements and component groups such as, for example, the position of the collimating optics 13, pinholes 26 and the like (not shown in detail).

For example, the laser radiation that is coupled into the scanning device 8 is branched through a beam splitter 30, one of the branches being directed to an optoelectronic receiver 31, wherein a plurality of line filters 32 which are arranged on filter wheels and can be exchanged with one another by rotating the filter wheels and neutral filters 33 which can likewise be exchanged with one another are arranged in front of the optoelectronic receiver 31. The output of the receiver 31 is likewise applied to a signal input of the evaluation circuit 28. The filter wheels on which the line filters 32 and the neutral filters 33 are arranged are coupled with adjusting devices whose control inputs are connected with signal outputs of the driving device 29 (not shown in the drawing).

Figure 2:
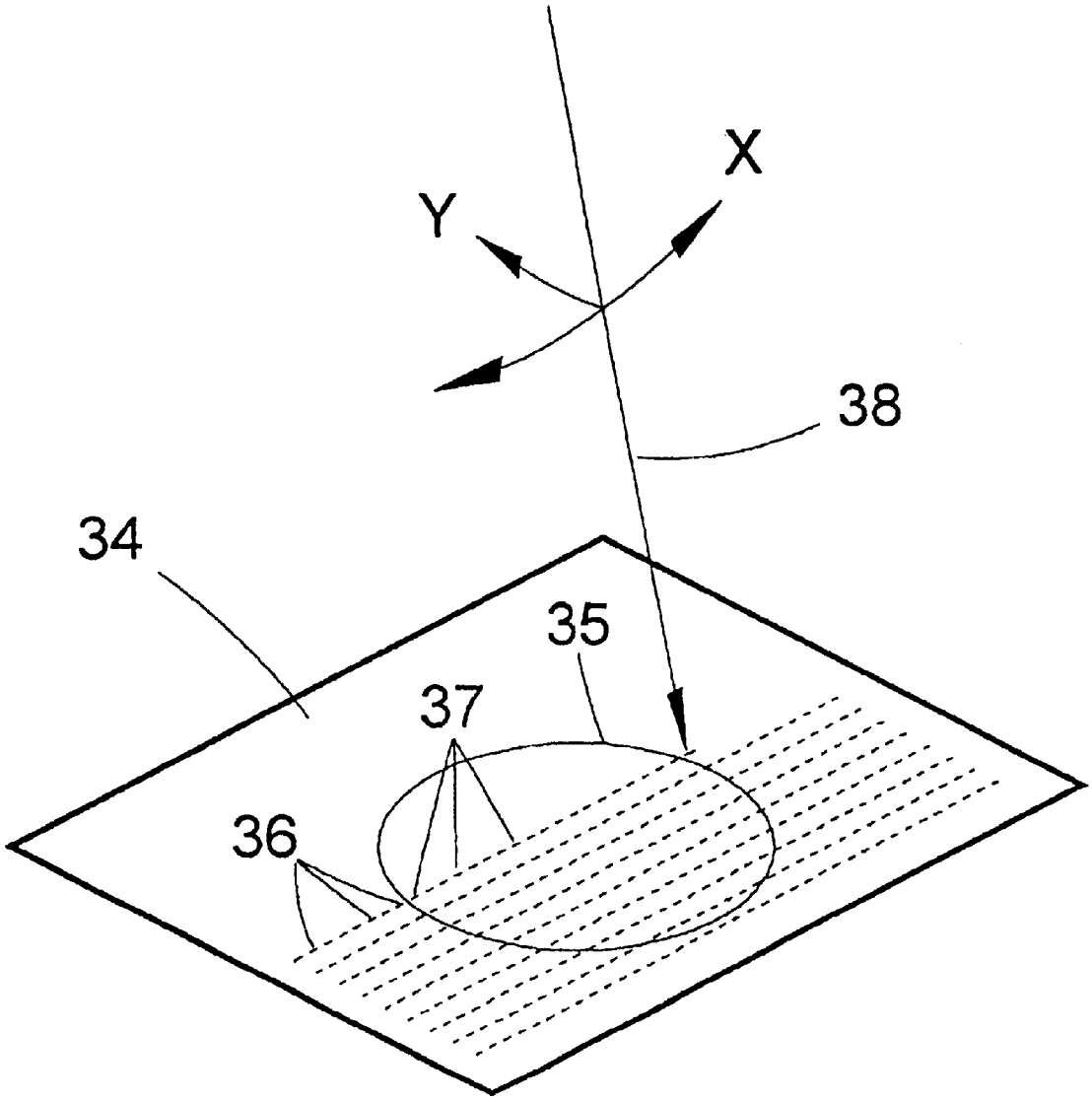
FIG. 2 shows a schematic illustration of the deflection of the laser light over the individual locations of a specimen.

During operation of the laser scanning microscope, the optical axis 38 of the microscope beam path is guided through the scanning device 8, as is illustrated in FIG. 2, in the direction of coordinate X from location to location and in the direction of coordinate Y from line to line in a raster pattern over the object plane 34 to be scanned, wherein the detail 35 of a specimen which is to be evaluated lies in this object plane 34.

In the prior art, laser light was previously coupled into the microscope beam path with a spectral composition and intensity which remained the same during scanning. As a result, a high radiation loading was necessary throughout in order to acquire images with sufficient brightness contrast or phase contrast, especially in high-resolution structure analyses of extremely low-contrast objects, for example, individual cells, organelles, organisms or parasites.

In order to reduce radiation loading while nevertheless increasing the quality of image evaluation, it is provided, according to the invention, that during the scanning of a line and/or of the object plane 34 the coupling in of individual spectral components or a plurality of spectral components or of the entire spectrum, as the case may be, is occasionally interrupted or, alternatively, individual spectral components or a plurality of spectral components are occasionally coupled in additionally.

The beam-deflecting device 9 remains active continuously during the change in the spectral composition or intensity of the laser light. In this way, for example, locations 36 and 37 within a scanning line or within the specimen to be scanned are acted upon differently. Therefore, it is possible for locations 37 which lie within the detail 35 to be evaluated, for example, in a cell, to be subjected to less radiation.

Conversely, an increase in the intensity and/or a change in the spectrum of the laser radiation is carried out during the scanning of location 37 when this is desirable, for example, when applying the process according to the invention for the purpose of photobleaching, wherein selected areas of the specimen are to be illuminated with a very high radiation intensity so as to be able to track the dynamic processes taking place immediately thereafter.

By means of the process according to the invention and the arrangement according to the invention, it is further possible to receive the light reflected and/or emitted by each individual irradiated location 36 and 37 in the individual detection channels 22, wherein each individual detection channel 22 is modified for receiving different spectral components of the light proceeding from the respective location.

A distinctive feature of the process according to the invention consists in that the detection and the evaluation of the light proceeding from every irradiated location is carried out synchronously with the irradiation of the location in question. To this extent, the excitation wavelength and the emission wavelength can be evaluated for each individual location 36 and 37 of the specimen and conclusions can be derived therefrom concerning the characteristics of the specimen at precisely the observed location.

It is also possible with the arrangement according to the invention to continuously monitor the composition and intensity of the laser light directed on the specimen based on the signals emitted by the optoelectronic receiver 31 and to utilize these signals for compensating for even very small variations in intensity via the driving device 29.

The excitation radiation and emission radiation which apply to one and the same location are evaluated by a computing circuit integrated in the evaluation circuit 28. In this way, it can be exactly determined whether a change in the emission wavelength or in the intensity of the emitted radiation which goes beyond a predetermined threshold has taken place during the deflection of the laser beam from one location to the other, for example, from directly adjacent locations 36 and 37. If such a change is noted, it may be concluded that an optical boundary layer is present in the adjacent locations 36 and 37.

Since the data of the deflection positions in the driving device 29 and/or in the evaluation circuit 28 are available for these locations 36, 37 and for every other scanned location on the specimen, the configuration of optical boundary layers of the type mentioned above can be determined by the process according to the invention on the basis of relevant deflection positions and, finally, the area or volume which is enclosed by the optical boundary layers can be calculated based on these deflection positions.

For the sake of completeness, it is noted that the object plane 34 shown in FIG. 2 refers only to one scanning plane of the specimen. It is possible, of course, to scan a plurality of planes of the specimen in that the laser radiation is focussed on different coordinates in the z-direction, i.e., vertical to the displayed surface.

While the foregoing description and drawings represent the preferred embodiments of the present invention, it will be obvious to those skilled in the art that various changes and modifications may be made therein without departing from the true spirit and scope of the present invention.

REFERENCE NUMBERS

1 laser module
2–4 lasers
5 beam combiner
6 AOTF
7 light-conducting fiber
8 scanning device
9 beam-deflecting device
10 laser module
11 AOTF
12 fibers
13 collimating optics

14 scanning objective
15 microscope
16 specimen
17 tubelens
18, 20 beam splitter
19 microscope objective
21 imaging optics
22 detection channels
23 photomultiplier (pmt)
24 deflecting prism
25 dichroitic beam splitter
26 pinholes
27 emission filter
28 evaluating unit
29 driving device
30 beam splitter
31 optoelectronic receiver
32 line filter
33 neutral filter
34 object field
35 detail
36, 37 locations
38 optical axis of the deflected microscope beam path

What is claimed is:

1. A process for confocal microscopy comprising the steps of:

coupling the laser light of different spectral ranges into a microscope beam path deflected in at least two coordinates and directing it successively with respect to time onto locations of a specimen;

permitting the specimen to be acted upon, location by location and line by line, by the laser light in at least one plane and generating an image of the scanned plane from light returned from the irradiated locations;

changing at least one of the spectral composition and the intensity of the laser light coupled into the microscope beam path while the deflection is continued without interruption, so that at least two adjacent locations of the specimen are acted upon by light of at least one of different spectral characteristics and different intensity.

2. The process for confocal microscopy according to claim 1, wherein at least one of the spectral composition and the intensity of the laser light is changed during the deflection by occasional additional coupling in of one of individual spectral components and of a plurality of spectral components and by occasional interruption of the coupling in of individual spectral components and of a plurality of spectral components.

3. The process for confocal microscopy according to claim 1, wherein the coupling in of the laser light is occasionally interrupted during the deflection.

4. The process for confocal microscopy according to claim 1, wherein at least one of the spectral composition and intensity of the laser light is changed during deflection on locations which are located adjacent to one another in a line, so that at least locations of this line are acted upon by laser radiation with at least one different spectral characteristics and different intensity.

5. The process for confocal microscopy according to claim 2, wherein the locations located adjacent to one another in a line are acted upon repeatedly by the coupled in laser light and, in this way, always the same locations are exposed to laser light with different spectral composition and/or with different intensity.

6. The process for confocal microscopy according to claim 1, wherein spectral components with wavelengths $\lambda_{A1}$=633 nm, $\lambda_{A2}$=568 nm, $\lambda_{A3}$=543 nm, $\lambda A_{A4}$=514 nm, $\lambda_{A5}$=488 nm and/or $\lambda_{A6}$=458 nm in the VIS range and with wavelengths $\lambda_{A7}$=351 nm and/or $\lambda_{A8}$=364 nm in the UV range are occasionally coupled in additionally or their coupling in is occasionally interrupted.

7. The process for confocal microscopy according to claim 1, wherein the light returned by every individual irradiated location of the specimen is evaluated with respect to its spectral characteristics and its intensity, wherein the evaluation is carried out synchronously in time with the irradiation of the same location and while taking into account at least one of the spectral composition and intensity of the laser light by which this location was irradiated.

8. The process for confocal microscopy according to claim 7, wherein the laser light returned by every individual irradiated location is detected with a plurality of detection channels, wherein the individual detection channels are arranged for receiving different spectral components.

9. The process for confocal microscopy according to claim 1, wherein at least one of the spectral composition and the intensity of the laser light which is coupled into the microscope beam path corresponds to the excitation radiation of a fluorescence dye contained in the specimen or applied to the specimen and the individual detection channels are configured for the reception of the emission radiation proceeding from the fluorescence dye.

10. The process for confocal microscopy according to claim 1, wherein a mathematical linking of data characterizing at least one of the spectral composition and the intensity of the laser light directed on a location, of data of the evaluation findings for the light returned by the same location and of the deflection positions corresponding to this location is carried out for the purpose of determining adjustment signals for changing at least one of the spectral composition and the intensity of the laser light directed on this location.

11. A laser scanning microscope for carrying out a process for confocal microscopy comprising the steps of:

coupling the laser light of different spectral ranges into a microscope beam path deflected in at least two coordinates and directing it successively with respect to time onto locations of a specimen;

permitting the specimen to be acted upon, location by location and line by line, by the laser light in at least one plane and generating an image of the scanned plane from light returned from the irradiated locations;

changing at least one of the spectral composition and the intensity of the laser light coupled into the microscope beam path while the deflection is continued without interruption, so that at least two adjacent locations of the specimen are acted upon by light of at least one of different spectral characteristics and different intensity, said microscope comprising:

a laser module for generating laser light with different selectable spectral components;

single-mode fibers for coupling the laser light into the microscope beam path;

a scanning device which deflects in at least two dimensions;

a microscope objective which focuses the laser light on a specimen;

a plurality of detectors for the reception of different spectral components of the light returned by the specimen;

an evaluation circuit which is connected subsequent to outputs of the detectors;

a plurality of individually controllable single-wavelength and multiple-wavelength lasers;

at least one of a filter which can be influenced acousto-optically and an acousto-optic modulator being provided in the laser module; photomultipliers being provided as detectors;

color splitters which are arranged on drivable exchanging devices and which can be substituted for one another being provided for branching the reflection radiation and emission radiation proceeding from the specimen into individual detection channels; and control inputs of the laser module, scanning device and exchanging devices being connected with the outputs of the evaluation circuit.

12. The laser scanning microscope according to claim 11, wherein a beam component of the laser light coupled into the microscope beam path is directed on an optoelectronic receiver whose output is connected with the driving unit.

13. The laser scanning microscope according to claim 11, wherein a mathematical linking of the output signals of the optoelectronic receiver with at least one of the output signals of the PMT and the deflection signals for the scanning device being provided in the evaluation circuit.

*14. A process for confocal microscopy comprising the steps of:*

*coupling laser light of different spectral ranges into a microscope beam path deflected in at least two coordinates and directing the laser light successively with respect to time onto locations of a specimen;*

*irradiating the specimen, location by location and line by line, by the laser light in at least one plane and generating an image of the scanned plane from light returned from the irradiated locations;*

*changing both the spectral characteristics and the intensity of the laser light coupled into the microscope beam path while the deflection continues without interruption, so that at least two adjacent locations of the specimen are acted upon by light of both different spectral characteristics and different intensities.*

*15. The process for confocal microscopy according to claim 14, wherein the spectral characteristics and the intensity of the laser light are changed during the deflection by at least one of (a) occasional additional coupling in of at least one of (1) individual spectral components and (2) a plurality of spectral components and (b) occasional interruption of the coupling in of at least one of (1) individual spectral components and (2) a plurality of spectral components.*

*16. The process for confocal microscopy according to claim 14, wherein the coupling in of the laser light is occasionally interrupted during the deflection.*

*17. The process for confocal microscopy according to claim 14, wherein the spectral characteristics and intensity of the laser light are changed during deflection on locations which are located adjacent to one another in a line, so that at least locations of this line are acted upon by laser radiation with different spectral characteristics and different intensities.*

*18. The process for confocal microscopy according to claim 15, wherein the locations located adjacent to one another in a line are acted upon repeatedly by the coupled in laser light and, in this way, the same locations are always exposed to laser light with different spectral characteristics and different intensities.*

*19. The process for confocal microscopy according to claim 14, wherein spectral components with wavelengths* $\lambda_{A1}$*=633 nm,* $\lambda_{A2}$*=568 nm,* $\lambda_{A3}$*=543 nm,* $\lambda A_{A4}$*=514 nm,* $\lambda_{A5}$*=488 nm and/or* $\lambda_{A6}$*=458 nm in the VIS range and with wavelengths* $\lambda_{A7}$*=351 nm and/or* $\lambda_{A8}$*=364* nm in the UV range are additionally occasionally coupled in.

*20. The process for confocal microscopy according to claim 14, wherein the coupling in of spectral components with wavelengths* $\lambda_{A1}$*=633 nm,* $\lambda_{A2}$*=568 nm,* $\lambda_{A3}$*=543 nm,* $\lambda A_{A4}$*=514 nm,* $\lambda_{A5}$*=488* nm and/or $\lambda_{A6}$*=458 nm in the VIS range and with wavelengths* $\lambda_{A7}$*=351 nm and/or* $\lambda_{A8}$*=364 nm in the UV range is occasionally interrupted.*

*21. The process for confocal microscopy according to claim 14, wherein the light returned by every individual irradiated location of the specimen is evaluated with respect to its spectral characteristics and its intensity, and wherein the evaluation is carried out synchronously in time with the irradiation of the same location and while taking into account at least one of the spectral characteristics and intensity of the laser light by which this location was irradiated.*

*22. The process for confocal microscopy according to claim 21, wherein the laser light returned by every individual irradiated location is detected with a plurality of detection channels, and wherein the individual detection channels are arranged for receiving different spectral components.*

*23. The process for confocal microscopy according to claim 14, wherein at least one of the spectral characteristics and the intensity of the laser light which is coupled into the microscope beam path corresponds to the excitation radiation of a fluorescence dye contained in the specimen or applied to the specimen and the individual detection channels are configured for the reception of the emission radiation proceeding from the fluorescence dye.*

*24. The process for confocal microscopy according to claim 14, wherein a mathematical linking of data characterizing at least one of the spectral characteristics and the intensity of the laser light directed on a location, of data of the evaluation findings for the light returned by the same location and of the deflection positions corresponding to this location is carried out for the purpose of determining adjustment signals for changing at least one of the spectral characteristics and the intensity of the laser light directed on this location.*

*25. A laser scanning microscope comprising:*

*means for generating laser light with different spectral components;*

*fibers coupling the laser light into a microscope beam path;*

*means for deflecting the laser light in at least two dimensions;*

*means for focusing the laser light on a specimen;*

*a plurality of detector means for receiving at least one of (a) different spectral components of the light returned by the specimen and (b) different spectral components of the light emitted by the specimen, each detector means being associated with a detection channel for one of a reflection band and an emission band;*

*means for quickly changing at least one of the spectral characteristics and the intensity of the laser light during the deflection of the laser light from location to location in an uninterrupted manner, whereby at least two locations located next to one another on the specimen are acted upon by at least one of light with different spectral characteristics and laser light of different intensity;*

*means for branching the reflection radiation and emission radiation proceeding from the specimen into individual detection channels; and*

*means for synchronously driving the means for quickly changing at least one of the spectral characteristics and the intensity of the laser light and the means for deflecting the laser light.*

*26. The laser scanning microscope according to claim 25, wherein the means for quickly changing includes at least one of (a) means for periodically interrupting coupling in of at least one of (1) individual spectral components and (2) a plurality of spectral components and (3) the radiation of the laser light in its entirety and (b) means for periodically coupling into the microscope beam path at least one of individual spectral components and a plurality of spectral components.*

*27. The laser scanning microscope according to claim 25, wherein the means for quickly changing at least one of the spectral characteristics and the intensity of the laser light comprises at least one of a filter which can be influenced acousto-optically and an acousto-optic modulator.*

*28. The laser scanning microscope according to claim 25, wherein the different spectral components are selectable.*

*29. The laser scanning microscope according to claim 25, wherein the means for branching comprise color splitters.*

*30. The laser scanning microscope according to claim 25, further comprising means for evaluating the light returned by every individual irradiated location of the specimen with respect to its spectral characteristics and its intensity synchronously in time with the irradiation of the same location and while taking into account at least one of the spectral characteristics and intensity of the laser light by which this location was irradiated.*

*31. The laser scanning microscope according to claim 30, further comprising means for mathematically linking data characterizing at least one of the spectral characteristics and the intensity of the laser light directed on a location with data from the evaluation means and with the deflection positions corresponding to this location, for determining adjustment signals for changing at least one of the spectral characteristics and the intensity of the laser light directed on this location.*

*32. A laser scanning microscope comprising:*

*means for generating laser light with different spectral components;*

*fibers coupling the laser light into a microscope beam path;*

*means for deflecting the laser light in at least two dimensions;*

*means for focusing the laser light on a location of a specimen;*

*a plurality of detector means for receiving (a) different spectral components of the light returned by the specimen and (b) different spectral components of the light emitted by the specimen, each detector means being associated with a detection channel for one of a reflection band and an emission band;*

*means for quickly changing both the spectral characteristics and the intensity of the laser light while the laser light is deflected from location to location in an uninterrupted manner, so that at least two locations located next to one another on the specimen are acted upon by light with different spectral characteristics and laser light of different intensity;*

*means for branching the reflection radiation and emission radiation proceeding from the specimen into individual detection channels; and*

*means for synchronously driving the means for quickly changing both the spectral characteristics and the intensity of the laser light and the means for deflecting the laser light.*

*33. The laser scanning microscope according to claim 32, wherein the means for quickly changing includes at least one of (a) means for periodically interrupting coupling in of at least one of (1) individual spectral components and (2) a plurality of spectral components and (3) the radiation of the laser light in its entirety and (b) means for periodically coupling into the microscope beam path at least one of individual spectral components and a plurality of spectral components.*

*34. The laser scanning microscope according to claim 32, wherein the means for quickly changing both the spectral characteristics and the intensity of the laser light comprises at least one of a filter which can be influenced acousto-optically and an acousto-optic modulator.*

*35. The laser scanning microscope according to claim 32, wherein the different spectral components are selectable.*

*36. The laser scanning microscope according to claim 32, wherein the means for branching comprise color splitters.*

*37. The laser scanning microscope according to claim 32, further comprising means for evaluating the light returned by every individual irradiated location of the specimen with respect to its spectral characteristics and its intensity synchronously in time with the irradiation of the same location and while taking into account at least one of the spectral characteristics and intensity of the laser light by which this location was irradiated.*

*38. The laser scanning microscope according to claim 37, further comprising means for mathematically linking data characterizing the spectral characteristics and the intensity of the laser light directed on a location with data from the evaluation means and with the deflection positions corresponding to this location, for determining adjustment signals for changing both the spectral characteristics and the intensity of the laser light directed on this location.*

*39. A laser scanning microscope for carrying out a process for confocal microscopy comprising:*

*means for deflecting a microscope beam in at least two coordinates and directing the beam successively with respect to time onto locations of a specimen;*

*means for coupling laser light of different spectral ranges into the microscope beam;*

*means for irradiating the specimen with the laser light, location by location and line by line, in at least one plane;*

*means for generating an image of the scanned plane from light returned from the irradiated locations; and*

*means for changing at least one of the spectral characteristics and the intensity of the laser light coupled into the microscope beam path while the deflection is continued without interruption, so that at least two adjacent locations of the specimen are acted upon by light of at least one of different spectral characteristics and different intensity.*

*40. The laser scanning microscope according to claim 39, wherein the means for changing includes at least one of:*

*means for occasionally additionally coupling in of one of individual spectral components and of a plurality of spectral components and*

*means for occasionally interrupting the coupling in of individual spectral components and of a plurality of spectral components.*

*41. A laser scanning microscope for carrying out a process for confocal microscopy comprising:*

*means for deflecting a microscope beam path in at least two coordinates and directing it successively with respect to time onto locations of a specimen;*

*means for coupling laser light of different spectral ranges into the microscope beam;*

*means for permitting the laser light to act upon the specimen, location by location and line by line, in at least one plane;*

*means for generating an image of the scanned plane from light returned from the irradiated locations; and*

*means for changing both the spectral characteristics and the intensity of the laser light coupled into the microscope beam path while the deflection is continued without interruption, so that at least two adjacent locations of the specimen are acted upon by light of both different spectral characteristics and different intensity.*

*42. The laser scanning microscope according to claim 41, wherein the means for changing comprises at least one of:*

*means for occasionally additionally coupling one of individual spectral components and of a plurality of spectral components and*

*means for occasionally interrupting the coupling in of individual spectral components and of a plurality of spectral components.*

* * * * *

UNITED STATES PATENT AND TRADEMARK OFFICE

CERTIFICATE OF CORRECTION

PATENT NO. : RE41,666 E
APPLICATION NO. : 10/959949
DATED : September 14, 2010
INVENTOR(S) : Ulrich Simon et al.

It is certified that error appears in the above-identified patent and that said Letters Patent is hereby corrected as shown below:

Cancel the text beginning with "comprising the steps of:" at Column 10, line 39, and ending with "said microscope comprising:" at Column 10, line 54, and insert the following text in its place:

--[comprising the steps of: coupling the] *in which* laser light of different spectral ranges *is coupled* into a microscope beam path deflected in at least two coordinates and [directing it] *the laser light of different spectral ranges is directed* successively with respect to time onto locations of a specimen[;], [permitting] the specimen [to be] *is* acted upon, location by location and line by line, by the laser light in at least one plane and [generating] an image of the scanned plane *is generated* from light returned from the irradiated locations[;], [changing] at least one of the spectral composition and the intensity of the laser light coupled into the microscope beam path *is changed* while the deflection is continued without interruption, so that at least two adjacent locations of the specimen are acted upon by light of at least one of different spectral characteristics and different intensity, said microscope comprising:--

Signed and Sealed this
Seventeenth Day of May, 2011

David J. Kappos

David J. Kappos
*Director of the United States Patent and Trademark Office*